(12) United States Patent
Burkett et al.

(10) Patent No.: US 11,361,020 B2
(45) Date of Patent: Jun. 14, 2022

(54) SYSTEMS AND METHODS FOR STORING AND SELECTIVELY RETRIEVING DE-IDENTIFIED MEDICAL IMAGES FROM A DATABASE

(71) Applicant: Imaging Endpoints II LLC, Scottsdale, AZ (US)

(72) Inventors: Doug Dean Burkett, Phoenix, AZ (US); David Jose Marichal, Lakeland, FL (US); Andre A Burkett, Phoenix, AZ (US)

(73) Assignee: IMAGING ENDPOINTS II LLC, Scottsdale, AZ (US)

( * ) Notice: Subject to any disclaimer, the term of this patent is extended or adjusted under 35 U.S.C. 154(b) by 849 days.

(21) Appl. No.: 15/684,866

(22) Filed: Aug. 23, 2017

(65) Prior Publication Data
US 2018/0276248 A1 Sep. 27, 2018

Related U.S. Application Data

(60) Provisional application No. 62/474,622, filed on Mar. 22, 2017.

(51) Int. Cl.
| | | |
|---|---|---|
| *G06F 21/62* | (2013.01) | |
| *G06F 16/58* | (2019.01) | |
| *G16H 15/00* | (2018.01) | |
| *G16H 50/20* | (2018.01) | |
| *G06F 16/54* | (2019.01) | |
| *G06F 16/33* | (2019.01) | |

(Continued)

(52) U.S. Cl.
CPC ...... *G06F 16/5866* (2019.01); *G06F 16/3344* (2019.01); *G06F 16/54* (2019.01); *G06F 21/6254* (2013.01); *G16H 15/00* (2018.01); *G16H 30/20* (2018.01); *G16H 50/20* (2018.01); *G16H 50/70* (2018.01)

(58) Field of Classification Search
CPC .......... G06F 19/30–321; G06F 21/6245–6254
USPC ....................................................... 707/736
See application file for complete search history.

(56) References Cited

U.S. PATENT DOCUMENTS

| | | |
|---|---|---|
| 6,434,569 B1 | 8/2002 | Toshimitsu et al. |
| 8,145,677 B2 | 3/2012 | Al-Shameri |
| 8,280,132 B2 | 10/2012 | Madabhushi et al. |

(Continued)

FOREIGN PATENT DOCUMENTS

| | | |
|---|---|---|
| EP | 1895468 A2 | 3/2008 |
| WO | 2015/023732 A1 | 2/2015 |

OTHER PUBLICATIONS

Wei, C. H., Li, C. T., & Wilson, R. (2005). A content-based approach to medical image database retrieval. In Database Modeling for Industrial Data Management: Emerging Technologies and Applications (pp. 284-291). IGI Global.

(Continued)

*Primary Examiner* — Robert W Beausoliel, Jr.
*Assistant Examiner* — Nirav K Khakhar
(74) *Attorney, Agent, or Firm* — Quarles & Brady LLP (57) ABSTRACT

A method of retrieving an image file from a first database, where the image file includes a link to an associated report stored in a second database. The method includes: de-identifying the report; applying a search query to the second database; returning the report in response to the applied query; applying the link to the first database; and returning the image file in response to the applied link.

20 Claims, 3 Drawing Sheets

(51) Int. Cl.
*G16H 30/20* (2018.01)
*G16H 50/70* (2018.01)

(56) References Cited

U.S. PATENT DOCUMENTS

| | | | |
|---|---|---|---|
| 9,390,236 B2 | 7/2016 | Geller et al. | |
| 2003/0013951 A1 | 1/2003 | Stefanescu et al. | |
| 2006/0010013 A1* | 1/2006 | Yamatake | G06F 16/583 |
| | | | 705/2 |
| 2006/0083442 A1* | 4/2006 | Loukipoudis | G06F 19/321 |
| | | | 382/305 |
| 2007/0050216 A1* | 3/2007 | Wright | H04N 1/00127 |
| | | | 705/3 |
| 2007/0160275 A1 | 7/2007 | Sathyanarayana | |
| 2010/0042653 A1* | 2/2010 | Krishnan | G16H 30/20 |
| | | | 715/205 |
| 2014/0019128 A1* | 1/2014 | Riskin | G06Q 10/06 |
| | | | 704/235 |
| 2016/0292241 A1* | 10/2016 | Patterson | G06F 16/254 |
| 2016/0342738 A1* | 11/2016 | Stalling | G06F 19/321 |

OTHER PUBLICATIONS

Hopp, Alix, Effectiveness of Using Texture Analysis in Evaluating Heterogeneity in Breast Tumor and in Predicting Tumor Aggressiveness in Breast Cancer Patients, The University of Arizona, Electronic Thesis, Mar. 25, 2016, pp. 1-53.

Fathabad, Y. F., & Balafar, M. A. (2012). Content based image retrieval for medical images. International Journal on Technical and Physical Problems of Engineering (IJTPE), (12), 177-182.

\* cited by examiner

SYSTEMS AND METHODS FOR STORING AND SELECTIVELY RETRIEVING DE-IDENTIFIED MEDICAL IMAGES FROM A DATABASE

TECHNICAL FIELD

The present invention relates, generally, to the selective identification and retrieval of image data files in response to a search query and, more particularly, to techniques for indirectly identifying responsive image data files by exploiting their association with corresponding clinical reports.

BACKGROUND

Digital image files are essentially an ordered matrix of grey scale values for a large number of pixels (or voxels) representing the relevant human anatomy under inspection, and are thus rich in data yet sparse with respect to information which can be conveniently harvested using traditional searching protocols. That is, each grey scale value (or other gradient or data parameter) encodes a wealth of patient biology and pathology, yet these data cannot be efficiently and accurately extracted unless and until they are subjectively evaluated and interpreted by a radiologist. Attempts to index or otherwise characterize image data files to render them searchable, while contemplated by the present invention, have had limited success.

Figure 1:
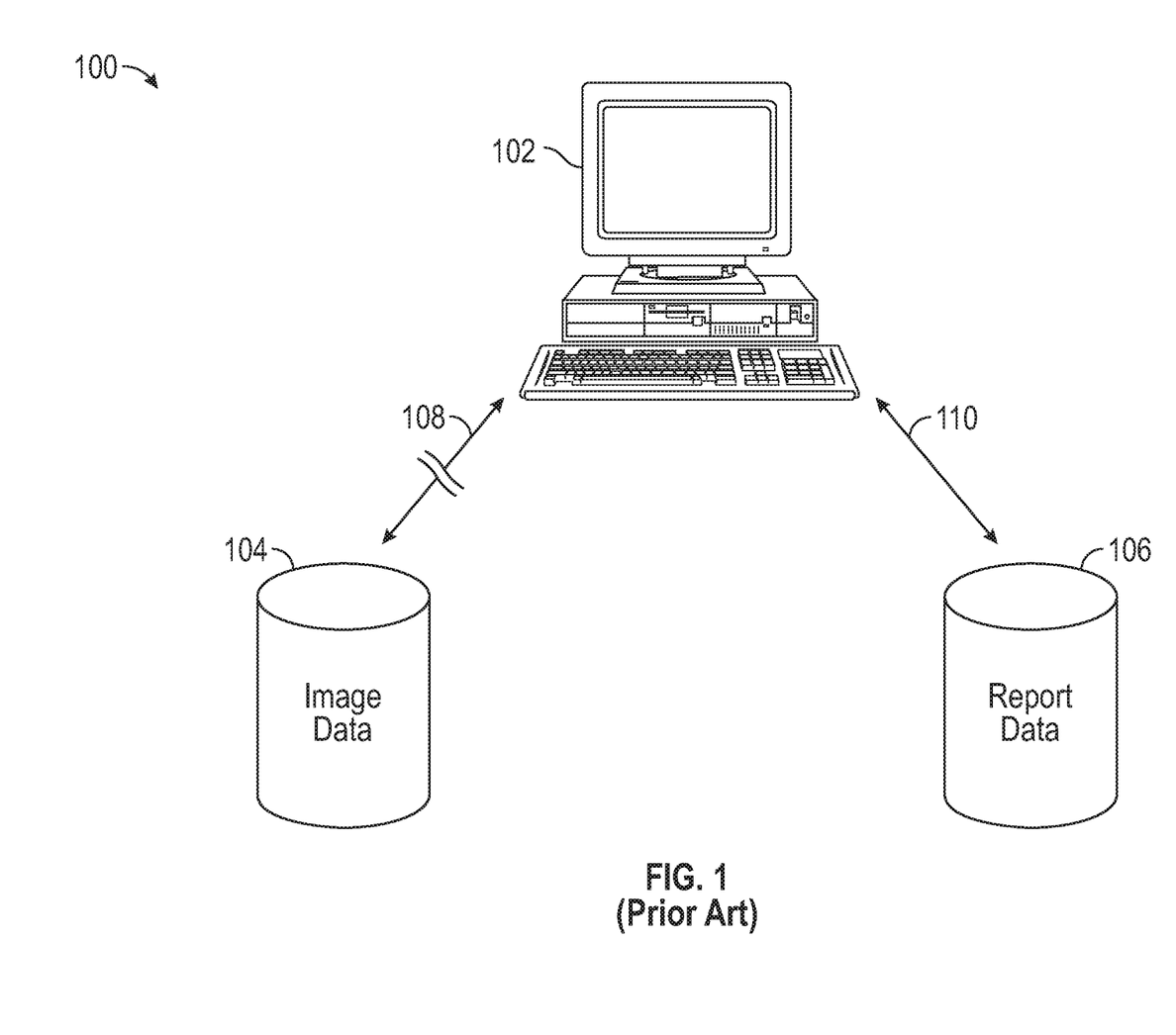
FIG. 1 is a schematic representation of an exemplary storage and retrieval system according to the prior art.

With reference to FIG. 1, a schematic representation of an exemplary prior art storage and retrieval system 100 includes a research terminal 102 configured to perform search requests, an image database 104 (or image database sector or partition), and a report database 106 (or report database sector or partition). The respective image and report data sectors are referred to as discrete "silos," because the image data and report data are stored and managed using different (often mutually exclusive) protocols which do not effectively communicate with each other.

The broken communication link 108 between the search terminal 102 and the image database 104 represents a limited ability to effectively retrieve images responsive to search queries. Specifically, queries typically must be performed against DICOM tags (metadata) associated with the images, but this approach is limited because the metadata typically does not include clinical findings or conclusions.

The reports, on the other hand, typically include the radiologist's findings and conclusions, albeit often in the form of unstructured text. Hence, the broken communication link 110 between the search terminal 102 and the report database 106 suggests that a back-end structured query language or other database reporting tool is typically required in order to perform key-word searches against corresponding tables containing the free text data in a database. This tends to be cumbersome, resource intensive, and generates a large number of false-positives.

Systems and methods are thus needed which overcome these limitations.

BRIEF SUMMARY

The present invention relates to systems and methods for effectively identifying and returning data files (e.g., medical images) responsive to search protocols of the type traditionally applied to text-based databases. Various embodiments of the present disclosure relate to systems and methods for:

i) Collecting a large number of radiology interpretations (reports) from a source site using HL7 migration. The reports may be imported individually or in bulk (batch processed), for example in HL7 ORU format. The reports may contain the clinical information (e.g., key words) and indexing attributes (e.g., Accession Number) used to identify corresponding medical image files in response to a request from a research analyst; that is, the reports may be configured to include information in a structured format which is responsive to search queries. The reports are stored in the Digital Imaging and Communications in Medicine (DICOM) Vendor Neutral Archive (VNA) database for future use and can be matched to their corresponding medical images later.

ii) As the reports are integrated into the database, patient identification information (PHI) is stripped out of them through a combination of predetermined de-identification of fields known to contain PHI, and programmed logic used to search the free text segments (OBX)) of the ORU message for key words to be removed. Alternatively, the reports and/or image files may be de-identified subsequent to (or during) searching and retrieval.

iii) The de-identified ORU is fed into an analytics engine and converted into structured HL7 CDA (clinical document architecture) that is encoded in a manner which facilitates subsequent data mining, such as through natural language processing (NLP) techniques.

iv) Queries are run against the analytics database to return a specific list of exams (reports and their associated images) based on specific criteria.

v) The returned list of exams is then fed into the DICOM engine of the VNA. The list will trigger a specific DICOM C-Find/C-Move event that pulls the requested exams as a bulk migration of DICOM studies from the image database source.

vi) As the studies migrate into the VNA, the DICOM tags containing PHI are stripped and the images are matched to the radiology reports in the database.

vii) Medical images and their corresponding reports are thus made available for research through various retrieval modalities including: a) conventional DICOM and HL7 migration methods; b) web based applications such as those employing an interactive graphical user interface (GUI); and c) web services (RESTful API's) via DICOM Web-RS and HL7 FHIR.

Various features and characteristics will also become apparent from the subsequent detailed description, taken in conjunction with the accompanying drawings and this background section.

BRIEF DESCRIPTION OF THE DRAWING FIGURES

Exemplary embodiments will hereinafter be described in conjunction with the following drawing figures, wherein like numerals denote like elements, and.

DETAILED DESCRIPTION OF PREFERRED EXEMPLARY EMBODIMENTS

The following detailed description of the invention is merely exemplary in nature and is not intended to limit the invention or the application and uses of the invention. Furthermore, there is no intention to be bound by any theory presented in the preceding background or the following detailed description.

Various embodiments of the present invention are described in the context of medical imaging data files and DICOM and HL7 protocols; however, those skilled in the art will appreciate that these descriptions are merely illustrative, and that the techniques described herein are agnostic a to any particular imaging modality, data content, and protocols for formatting, storing, retrieving, and associating the data files with corresponding information files to facilitate searching. For example, the data files linked to the reports may include, in addition to or in lieu of medical images, clinical data such as blood work results, pathology, gastrointestinal (GI) test results, endoscopy, or imaging macrophages within a tumor, particularly if there are one or more links to a searchable document, a traditional radiological image, or both.

Although various embodiments are described in the context of RIS and HIS reports, it will be understood that the inventions described herein contemplate any report type or format from any system containing diagnostic or interpretive results. Likewise, report data need not be structured in an HL7 format but may include other data formats such as xml, csv, and other formats currently used or hereafter adopted.

Moreover, it is possible within the bounds of the invention to link radiology reports to their associated DICOM or other images without an accession number, such as if the files are linked using date and time of exam, alone or in combination with one or more additional identifying metrics such as patient name, Medical Record Number (MRN), and the like.

The present disclosure further contemplates linking non-radiology reports to radiology images by means other than an accession number, particularly when the numbers are not the same (e.g. a pathology report will not have the same accession number as the radiology report or the DICOM image even if the test was requested by the radiologist in the radiology report). Accordingly, the invention contemplates "loosely" linking reports to corresponding images via means other than accession number, such as MRN.

The present disclosure further contemplates searching directly linked radiology reports along with "loosely" linked medical data to return images. For example, one may search for patients with low blood pressure (lab report) and who have lung tumors (radiology report), and view images that meet both criteria.

In the context of the present disclosure, the term "exam" typically refers to some version of the following sequence of inter-related events: i) performing a radiological procedure on a patient by a medical technician; ii) generating a data file representing the medical image obtained during the radiological procedure; iii) performing a review and analysis of the resulting medical image by a medical professional (e.g., a radiologist); iv) preparing a written report (usually digital) by the radiologist memorializing the salient aspects of the review and analysis (particularly diagnostic observations); and v) generating a unique exam identifier, referred to herein as an Accession Number or "ACC #," which associates (or links) the written report with the underlying medical image upon which the report is based.

The present inventors recognized that the very nature of medical image data files is inherently antithetical to traditional key word and/or key attribute searching. That is, the raw data must be interpreted—either subjectively by a human or programmatically (e.g., algorithmically) by a machine—before the data can be effectively searched. The present inventors also determined that applying indices to a data file, or defining a scheme of attributes to characterize a data file to facilitate searching, is a cumbersome, subjective, and computationally intensive undertaking. Accordingly, the present inventors propose an indirect approach to selectively identifying image data files which are contemplated by or responsive to presently known (and hereafter developed) query protocols.

By way of non-limiting example, a traditional key word based query may be applied as an argument to that portion of the database which contains the reports. Indeed, the didactic nature of the reports makes them well suited to key word based queries. Upon identifying a set of reports responsive to the search request, the unique exam identifier associated with each report allows the corresponding image data files to be efficiently and unambiguously identified, assembled, and returned with the search results. Thus, for all intents and purposes a researcher may employ familiar semantics to formulate familiar structured query strings and thereby "search" an image database; the notion that the query may actually be applied to the report sector of the database (as opposed to the image data sector), and the corresponding images subsequently "bootstrapped" to the responsive reports using the linking ACC #, is largely transparent to the searcher.

It is worth noting that medical reports and medical image data typically include the patient's personal health information (sometimes referred to as Protected Health Information (PHI) or Personally Identifiable Information (PII)). Thus, in this context, it may be appropriate and perhaps even necessary and to remove ("de-identify") the PHI from the responsive reports and/or images to protect patient confidentiality. In the context of data retrieval applications which do not involve PHI, it may not be necessary or appropriate to remove attributes from the returned files; alternatively, depending on the nature of the application, it may be appropriate to remove, encrypt, or otherwise modify other attributes (e.g., national security, military, financial, or other sensitive data or information).

When a patient first enters an ambulatory outpatient or acute care inpatient facility, there is an initial patient registration process in which a patient record is created in the health care provider's data management system. The patient record typically includes the patient's demographic information (name, SSN, address, email, phone number, billing information, etc.). Many medical centers currently store patient demographics and exam scheduling information in an HIS (Hospital Information Systems) or RIS (Radiology Information Systems) system. During a subsequent image acquisition phase (e.g., mammogram, chest X-ray), rather than manually re-entering the patient's demographics on the modality's console, the DICOM modality worklist service allows for an automated, reliable, error-free transfer of the information stored in the HIS/RIS directly to the modality, in a standard way which is supported by most DICOM modalities. As the patient's demographic information subsequently flows downstream into cardiac, radiological, and other systems during the patient's health care delivery life cycle, the patient's PHI flows with it.

For example, a health care provider may order a procedure (e.g., a pre-operative chest X-ray), using a CPOE (computerized physician order entry) or other ordering system. When the order is sent to the radiology information system, the patient's demographics (including PHI) are sent along with or as part of the order. This is often the point at which an accession number (e.g., ACC #) is created and attached to the exam record. Alternatively, if the institution uses an enterprise ordering system which contemplates all procedures (as opposed to a dedicated ordering system for, say, radiological exams), the enterprise ordering system may be configured to generate the accession number.

A picture archiving and communication system (PACS) is a medical imaging technology which provides economical storage of and convenient access to images from multiple modalities (source machine types). PACS has an interface called the DICOM Modality Worklist which lists the patients scheduled for various procedures such as radiological exams. Each patient's original demographic information may be passed through to the work list for use by the technician performing the procedure (e.g., chest X-ray).

Once the images are produced, their corresponding data files are pushed into an archive (e.g., PACS/VNA) for later retrieval and interpretation by the radiologist to facilitate generation of the associated diagnostic report.

The radiologist opens and reviews each image, typically using an API linked to a DICOM viewer application (e.g., a PACS viewer or universal diagnostic viewer that communicates with the VNA). The radiologist then generates the report using a dictation application, text template, voice recognition system, or other tool. The ACC # and patient demographic information (including PHI) is typically passed from the PACS into the report automatically. In particular, the report rendering application (e.g., "Nuance" by Power scribe 360, "Fluency for Imaging" by M*Modal) may be configured to prompt the radiologist to input findings and conclusions (impressions) into the report template, such as clinical conditions and pathologies for the observed anatomy, and any associated analyses and diagnostic interpretations. The information may be input orally and/or through command navigation using an open, closed, or hybrid vocabulary set, the terms of which may be used to facilitate subsequent searching.

Once completed, the report is stored or otherwise linked back to the RIS (and/or the PACS/VNA) database. After being retrieved from the source database, the reports may be scrubbed and pushed (or pulled) into the VNA database and/or an analytics database for subsequent searching, as described below in conjunction with FIGS. 2 and 3.

Figure 2:
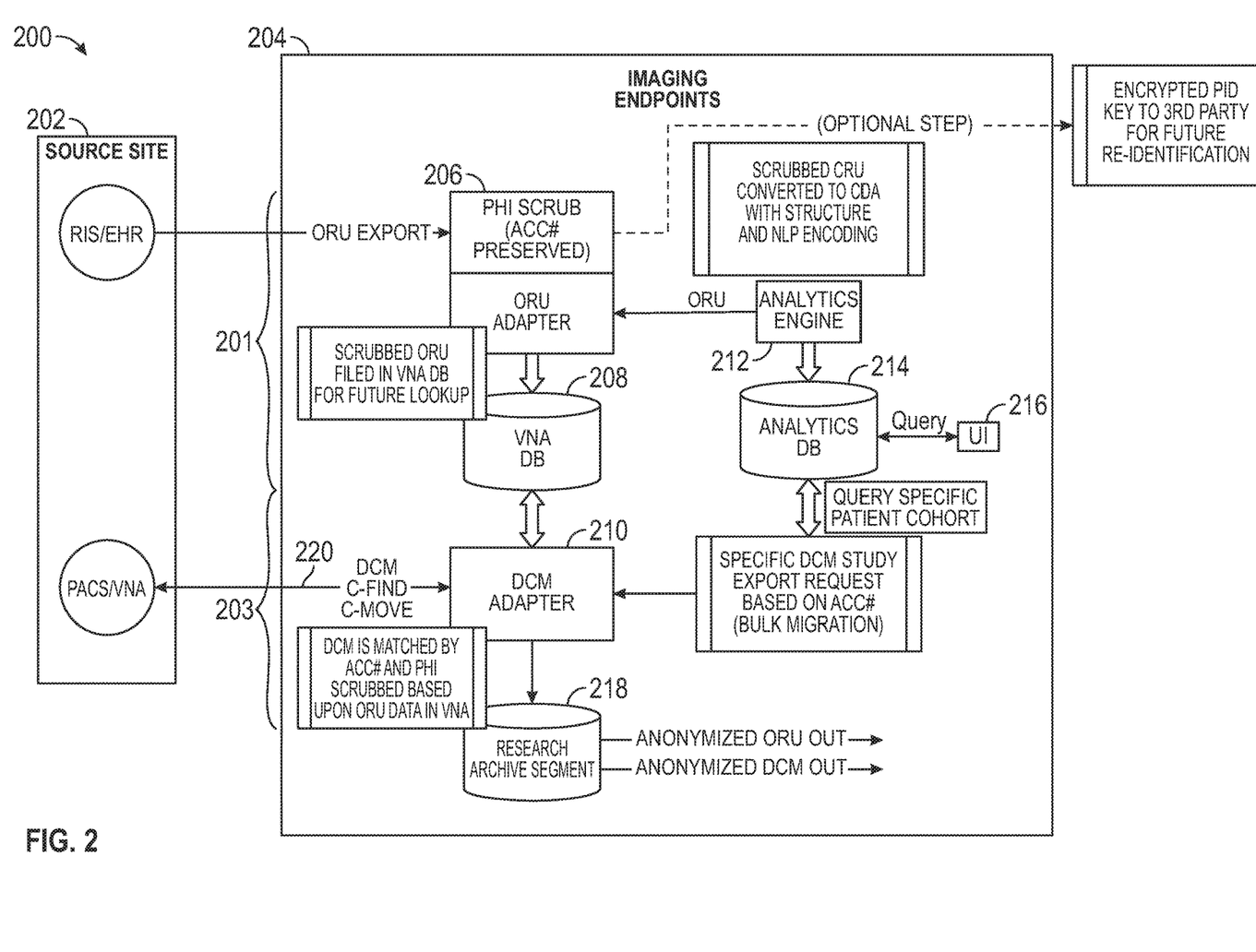
FIG. 2 is a schematic layout diagram of an exemplary system for storing and selectively retrieving, in response to search queries, report data and image data in accordance with the present invention.

Referring now to FIG. 2, various embodiments of the present invention enable researchers to employ familiar structured search techniques to identify and return image files responsive to a search query, by identifying responsive reports and also including the corresponding linked image files within the returned search results.

An exemplary system 200 for storing and selectively retrieving reports and corresponding images in response to a search request includes a source site 202, and a storage and retrieval subsystem 204 including a report formatting and storage subsystem 201 (above the dashed line), and an image retrieval subsystem 203 (below the dashed line).

More particularly, the source site 202 includes an ORU communication link extending between an RIS/Electronic Health Record (HER) database structure and a PHI scrub/ORU adapter 206, also referred to herein as a scrubber. The communication link may be configured to function as a real time (or near real time) data feed, a batch processing link, or both. In any event, information supplied via the communication link updates a VNA database 208 with exam data including, for each exam, one or more of a report file, an image file (discussed below in conjunction with the DICOM or DCM adapter 210), and a unique ACC # linking the report and its associated image or images to the unique exam identifier. In an embodiment, the reports are processed into the storage and retrieval subsystem 204 independently from the images. Alternatively, they may be processed into the system together.

The scrubber 206 de-identifies the report and/or image files, and imports the clean versions into the VNA database 208. In addition, the ORU adapter exports the scrubbed files (particularly the report files) to an analytics engine 212. Various software tools for scrubbing PHI may be configured to scrub both known PHI fields within the HL7 protocols, as well as unstructured text. The analytics engine may be configured to convert the ORU from its native ORU format into a CDA (Clinical Document Architecture) HL7 format to facilitate sharing, searching, and other desired interoperability.

In addition, the analytics engine may be configured to apply natural language processing (NLP) techniques to the data files to transform the free (unstructured) text into a structured format (e.g., XML) rendering the documents suitable for searching. To mitigate the "fire hose" of false positives during subsequent searching, the free text may be subjected to natural language processing, whereby clinical concepts are encoded into one or more radiology lexicons; terms within the lexicon may then be used to search for the underlying clinical conditions and concepts to retrieve the report. For example, the phrase "no evidence of malignancy" may be encoded to specifically indicate no malignancy, to avoid returning such reports in response to a request for reports indicating the presence of "malignancy".

In the illustrated embodiment, the analytics engine 212 reformats the report files into CDA, and loads the data into an analytics database 214, where it is exposed to search queries. In an embodiment, if implemented properly the NLP techniques may allow reports—and their corresponding images—to be returned in response to a key word search query even if the key words are not found in the responsive reports, to the extent the natural language concepts are properly coded.

With continued reference to FIG. 2, a user interface (UI) 216 is configured to allow a researcher to structure search queries and apply them to the analytics database 214. The analytics database 214 (and/or the analytics engine 212) processes the search request and returns a list of exams responsive to the request. In the illustrated embodiment, the system generates a custom export list (typically comprising ACC #s) and exposes the list to a custom DCM (DICOM) migration adapter 210. The adapter 210 then processes the list of exams (the search results) by interrogating a PACS/VNA (vendor neutral archive) database within the source site 202 which houses image files, whereupon the corresponding images are retrieved, de-identified by the DCM adapter 210, and linked back to their corresponding reports listed in the search results. Specifically, if the corresponding images are returned from the source 202, they are linked to their report files and placed into the VNA database 208, in the archive database 218, or both. After being retrieved, the responsive images (and/or the corresponding reports) may be PHI scrubbed, or at least appropriately anonymized.

The foregoing architecture allows the retrieval system to be implemented in any number of ways. For example, the report database may be searched and responsive exams returned along with their associated images. In an alternative embodiment, the report results may be returned along with their ACC # identifiers, whereupon the researcher or the research institution may separately obtain the images, as needed, from another source (for example, from their own proprietary image database).

With continued reference to FIG. 2, Health 7 International's (HL7) Fast Healthcare Interoperable Resource (FHIR) interoperability product facilitates the exchange of healthcare information among disparate applications and record keeping systems. A typical HL7 formatted message may include one or more of the following segments or fields: a message header which describes the type of message and information regarding the sending and receiving systems; and information describing the type of exam, why it was ordered, and the like. Some of the more common HL7 message types include:

ACK—General acknowledgement
ADT—Admit discharge transfer
BAR—Add/change billing account
DFT—Detailed financial transaction
MDM—Medical document management
MFN—Master files notification
ORM—Order (Pharmacy/treatment)
ORU—Observation result (unsolicited)
QRY—Query, original mode
RAS—Pharmacy/treatment administration
RDE—Pharmacy/treatment encoded order
RGV—Pharmacy/treatment give
SIU—Scheduling information unsolicited In addition, an HL7 formatted message also typically includes a patient ID field. Consequently, exam files transmitted from a source site to a storage and retrieval subsystem typically include at least one field containing PHI, such as the patient identifier (PID) segment and its corresponding fields. Thus, when the scrubber 206 de-identifies the images and/or reports, it looks to the PID fields likely to contain PHI, as defined by the HL7 protocols. In addition, the scrubber 206 may also use key word, natural language, and other techniques for identifying additional PHI to be scrubbed. In an embodiment, information and/or data (e.g., key words) obtained from the PID may be used to search the body of the report (e.g., the findings and conclusions) for additional PHI. By way of non-limiting example, if the name "John Smith" is found in the PID section, then the system may be configured to search for "John," "Smith," and/or "John Smith" in the findings section.

Figure 3:
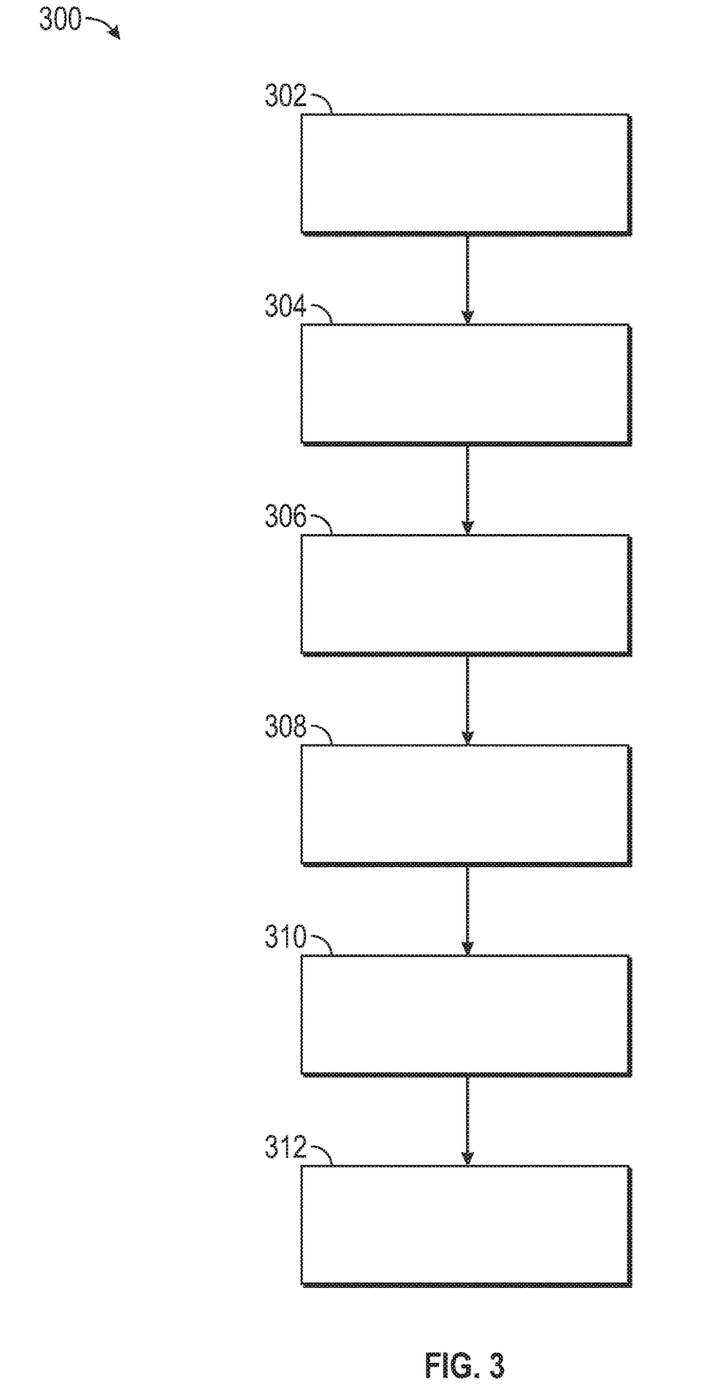
FIG. 3 is a flow chart illustrating a method of searching a report database and returning linked images in accordance with various embodiments.

Referring now to FIG. 3, an exemplary method 300 for effectively searching an image database includes generating a data (e.g., image) file and storing it in an image database (Task 302), retrieving the image and preparing a report summarizing findings and/or conclusions (Task 304), and storing the report in a report database (Task 306) with a link to its associates image(s). The method may also include removing or suppressing PHI from the image and/or the report (Task 308), and applying a search query to the report database (Task 310). Reports responsive to the query—and/or their linked images—may be returned to the searcher (Task 312).

In various embodiments, PHI may be scrubbed (de-identified) from the reports and/or images prior to, subsequent to, and/or during the search operation. Indeed, the system may arguably return more meaningful clinical research results if all or a substantial portion of the scrubbing/anonymizing is done after the search results are returned, thereby allowing the search queries to be applied using to the raw (un-scrubbed) source data (reports and images). By way of non-limiting example, if certain patient surnames, attending physicians, or scanner equipment manufacturers have a higher or lower correlation to a disease state, it may be desirable to search the raw data and anonymize or de-identify the results, rather than scrub the data prior to searching.

In various embodiments, the system may be configured to: i) partially or entirely forego de-identifying PHI, to facilitate more robust searching; ii) partially or fully de-identify PHI during or after searching is completed; iii) import source data (e.g., report files) which have already been partially or fully de-identified; iv) utilize a third party or system (outside the system comprising the source site 202 and the storage and retrieval subsystem 204) to perform de-identification; v) filter or refine the search results by searching DICOM tags (e.g., within the VNA) before, during, and/or after searching the report database; vi) use a single and/or enterprise wide user interface in lieu of the UI 216 and the archive database 218; vii) replace the VNA database 208 with a PACS.

A method is provided for retrieving an image file from a first database, the image file including a link to an associated report stored in a second database, the method including: de-identifying the report; applying a search query to the second database; returning the report in response to the applied query; applying the link to the first database; and returning the image file in response to the applied link.

In an embodiment, de-identifying comprises removing protected health information (PHI) from the report.

In an embodiment, the first database comprises an image database; and the second database comprises a report database separate from the image database.

In an embodiment, the first and second databases are geographically remote.

In an embodiment, the first and second databases comprise separate data sectors within the same database.

In an embodiment, the method further includes applying natural language processing (NPL) to the report prior to applying the search query.

In an embodiment, the search query is applied subsequent to de-identifying the report.

In an embodiment, the search query is applied prior to de-identifying the report.

In an embodiment, the method further includes importing the report into the second database from a source database in HL7 ORU format.

In an embodiment, the link comprises a Digital Imaging and Communications in Medicine (DICOM) compatible accession number (ACC #).

In an embodiment, the report is configured to be compliant with HL7 protocols; and de-identifying comprises using a software tool to scrub PHI from: i) PHI fields within the HL7 protocols; and ii) unstructured text within the report.

In an embodiment, the NLP is configured to convert the report from its native format into a Clinical Document Architecture (CDA) HL7 format to facilitate searching.

A system is also provided for selectively retrieving medical images responsive to a search query. The system includes: a first source database containing a plurality of image files; a second source database containing a plurality of report files, each report file including a link to a corresponding image file; a storage module including a scrubber an analytics engine, and an analytics database the storage module configured to communicate with the second source database; a retrieval module including a user interface, the retrieval module configured to communicate with the storage module and the first source database; and a processor. The processor may be configured to: import report files from the second source database into the storage module; de-identify the report files using the scrubber; apply natural language processing (NLP) to the reports and store the NLP processed reports in the analytics database; apply a search query from the user interface to the analytics database;

return a first report file responsive to the query, the first report file including a first link; interrogate the first source database using the first link; and return to the user interface a first image file associated with the first link.

In an embodiment, the first source database comprises a plurality of image files formatted in accordance with one of: i) a picture archiving and communication system (PACS); and ii) a vendor neutral archive (VNA) system compatible protocols; and the second source database comprises a plurality of report files formatted in accordance with one of a hospital information systems (HIS) and a radiology information systems (RIS) compatible protocols.

In an embodiment, the processor is configured to import the report files from the second source database into the storage module using HL7 compatible protocols.

In an embodiment, the processor may be configured to: interrogate the first source database using a DICOM C-Find compatible protocol; and return the first image file using a DICOM C-Move compatible protocol.

In an embodiment, the scrubber is configured to de-identify the report files using a software tool configured to scrub PHI from: i) PHI fields within the HL7 protocols; and ii) unstructured text within the reports.

In an embodiment, the first link comprises a DICOM compatible accession number (ACC #).

In an embodiment, the NLP is configured to convert the report from a native format into a Clinical Document Architecture (CDA) HL7 format to facilitate searching.

In an embodiment, the processor may be selectively configured to de-identify the report files before, during, or after applying the search query to the analytics database.

As used herein, the word "exemplary" means "serving as an example, instance, or illustration." Any implementation described herein as "exemplary" is not necessarily to be construed as preferred or advantageous over other implementations, nor is it intended to be construed as a model that must be literally duplicated.

While the foregoing detailed description will provide those skilled in the art with a convenient road map for implementing various embodiments of the invention, it should be appreciated that the particular embodiments described above are only examples, and are not intended to limit the scope, applicability, or configuration of the invention in any way. To the contrary, various changes may be made in the function and arrangement of elements described without departing from the scope of the invention as set forth in the appended claims.

The invention claimed is:

1. A method of retrieving an image file from a first database, the image file including a link to an associated report stored in a second database, the method comprising:
de-identifying the report;
applying a search query to the second database;
returning the report in response to the applied query;
applying the link to the first database; and
returning the image file in response to the applied link.

2. The method of claim 1, wherein de-identifying comprises removing protected health information (PHI) from the report.

3. The method of claim 1, wherein:
the first database comprises an image database; and
the second database comprises a report database separate from the image database.

4. The method of claim 1, wherein the first and second databases are geographically remote.

5. The method of claim 1, wherein the first and second databases comprises separate data sectors within the same database.

6. The method of claim 1, further comprising:
applying natural language processing (NPL) to the report prior to applying the search query.

7. The method of claim 1, wherein the search query is applied subsequent to de-identifying the report.

8. The method of claim 1, wherein the search query is applied prior to de-identifying the report.

9. The method of claim 1, further comprising:
importing the report into the second database from a source database in HL7 ORU format.

10. The method of claim 9, wherein the link comprises a Digital Imaging and Communications in Medicine (DICOM) compatible accession number (ACC #).

11. The method of claim 10, wherein:
the report is configured to be compliant with HL7 protocols; and
de-identifying comprises using a software tool to scrub PHI from: i) PHI fields within the HL7 protocols; and ii) unstructured text within the report.

12. The method of claim 6, wherein the NLP is configured to convert the report from its native format into a Clinical Document Architecture (CDA) HL7 format to facilitate searching.

13. A system for selectively retrieving medical images responsive to a search query, the system comprising:
a first source database containing a plurality of image files;
a second source database containing a plurality of report files, each report file including a link to a corresponding image file;
a storage module including a scrubber, an analytics engine, and an analytics database, the storage module configured to communicate with the second source database;
a retrieval module including a user interface, the retrieval module configured to communicate with the storage module and the first source database; and
a processor configured to:
import report files from the second source database into the storage module;
de-identify the report files using the scrubber;
apply natural language processing (NLP) to the reports and store the NLP processed reports in the analytics database;
apply a search query from the user interface to the analytics database;
return a first report file responsive to the query, the first report file including a first link;
interrogate the first source database using the first link; and
return to the user interface a first image file associated with the first link.

14. The system of claim 13, wherein:
the first source database comprises a plurality of image files formatted in accordance with one of: i) a picture archiving and communication system (PACS); and ii) a vendor neutral archive (VNA) system compatible protocols; and
the second source database comprises a plurality of report files formatted in accordance with one of a hospital information systems (HIS) and a radiology information systems (RIS) compatible protocols.

15. The system of claim 13, wherein the processor is configured to import the report files from the second source database into the storage module using HL7 compatible protocols.

16. The system of claim 13, wherein the processor is configured to:
   interrogate the first source database using a Digital Imaging and Communications in Medicine (DICOM) C-Find compatible protocol; and
   return the first image file using a DICOM C-Move compatible protocol.

17. The system of claim 16, wherein the scrubber is configured to de-identify the report files using a software tool configured to scrub PHI from: i) PHI fields within the HL7 protocols; and ii) unstructured text within the reports.

18. The system of claim 13, wherein the first link comprises a DICOM compatible accession number (ACC #).

19. The system of claim 13, wherein the NLP is configured to convert the report from a native format into a Clinical Document Architecture (CDA) HL7 format to facilitate searching.

20. The system of claim 13, wherein the processor may be selectively configured to de-identify the report files before, during, or after applying the search query to the analytics database.

\* \* \* \* \*